US008367742B2

(12) United States Patent
Vu et al.

(10) Patent No.: US 8,367,742 B2
(45) Date of Patent: *Feb. 5, 2013

(54) REMOVABLE COLOR LAYER FOR ARTIFICIAL NAIL COATINGS AND METHODS THEREFORE

(75) Inventors: Thong H. Vu, Vista, CA (US); Diane Marie Larsen, Carlsbad, CA (US); Chad Conger, San Marcos, CA (US); Douglas D. Schoon, Dana Point, CA (US)

(73) Assignee: Creative Nail Design, Inc., Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/303,584

(22) Filed: Nov. 23, 2011

(65) Prior Publication Data

US 2012/0083547 A1 Apr. 5, 2012

Related U.S. Application Data

(63) Continuation of application No. 12/573,633, filed on Oct. 5, 2009.

(51) Int. Cl.
*C08F 210/00* (2006.01)
*C08J 3/07* (2006.01)
*C08J 3/20* (2006.01)
*C08J 3/24* (2006.01)
*C08J 3/28* (2006.01)
*A61Q 3/02* (2006.01)

(52) U.S. Cl. .......... 521/149; 522/68; 522/114; 522/120; 523/105; 424/61

(58) Field of Classification Search .................. 521/144, 521/149; 523/105; 522/33, 64, 68, 114
See application file for complete search history.

(56) References Cited

U.S. PATENT DOCUMENTS

| 4,745,003 A | 8/1925 | Weeks |
| 4,813,875 A | 1/1930 | Kirlin |
| 4,844,102 A | 3/1933 | Proteau |
| 4,846,165 A | 2/1934 | Dellinger |
| 6,426,034 B1 | 4/1961 | Greenman |
| 3,297,664 A | 1/1967 | Usifer |
| 6,238,679 B1 | 1/1967 | Miskel |
| 3,629,187 A | 12/1971 | Bayless |
| 6,481,444 B1 | 12/1971 | Waller |
| 3,709,866 A | 1/1973 | Hoffman |
| 6,599,958 B2 | 1/1973 | Waller |
| 6,685,838 B2 | 12/1975 | Rosenberg |
| 6,750,277 B1 | 5/1978 | Dart |
| 4,158,053 A | 6/1979 | Greene et al. |
| 6,803,394 B2 | 11/1979 | Rowe |
| 6,818,207 B1 | 2/1980 | Schmitt |
| 4,721,735 A | 5/1980 | Nagasawa |
| 6,831,115 B2 | 10/1980 | Lee, Jr. |
| 1,548,497 A | 4/1981 | Lee, Jr. |
| 1,743,922 A | 12/1983 | Benkendorf |
| 1,900,761 A | 1/1984 | Nativi |
| 1,947,153 A | 4/1985 | Bowen |
| 6,355,599 B1 | 2/1986 | Maeda |
| 7,063,936 B2 | 6/1986 | Giuliano |
| 7,098,256 B2 | 7/1986 | Newman |
| 7,309,550 B2 | 5/1987 | Henne |
| 7,364,834 B2 | 7/1987 | Giuliano |
| 7,378,460 B2 | 9/1987 | Giuliano |
| 7,388,039 B2 | 1/1988 | Sensenbrenner |
| 7,514,477 B2 | 1/1988 | Bennett |
| 7,595,351 B2 | 5/1988 | Sirkoch |
| 7,615,283 B2 | 3/1989 | Hare |
| 7,649,058 B2 | 7/1989 | Repensek |
| 7,713,680 B2 | 7/1989 | Hare |
| 7,718,264 B2 | 9/1989 | Hare |
| 7,722,939 B2 | 12/1991 | Kubota |
| 7,806,050 B2 | 7/1992 | Mast |
| 5,173,288 A | 12/1992 | Everhart et al. |
| 4,572,888 A | 1/1993 | Hare |
| 5,958,951 A | 7/1993 | Pinchuk |
| 2,979,061 A | 5/1994 | Schlossman |
| 4,205,018 A | 7/1995 | Valenty |
| 3,928,113 A | 9/1995 | Sokol |
| 4,260,701 A | 10/1995 | Valenty |
| 4,421,881 A | 1/1996 | Usifer |
| 4,424,252 A | 5/1996 | Marr-Leisy |
| 4,089,763 A | 6/1997 | Thomas |
| 4,174,307 A | 9/1997 | Martin |

(Continued)

FOREIGN PATENT DOCUMENTS

EP 0356868 3/1990
EP 0453628 10/1991

(Continued)

OTHER PUBLICATIONS

Ebecryl 200 Data Sheet. Lookchem. 2008.*
Cheremisinoff, N.P. "Handbook of Hazardous Chemical Properties," Copyright 2000, Elsevier, p. 211.
International Search Report for PCT International Application No. PCT/US2010/147171, mailed Nov. 10, 2010.
Kumar, Sudesh G, et al., Biodegradation of gelatin-g-Poly (ethyl Acrylate) copolymers, 26 Journal of Applied Polymer Science, (1981) 3633-3641.
Physical Properties of Monomers, "Diurethane Dimethacrylate (isomers)." Polymer Handbook, 4th Edition, 1999, John Wiley & Sons.
Venz S. et al., Modified Surface-Active Monomers for Adhesive Binding to Dentin, vol. 72, No. 3 Journal of Dental Research, Mar. 1993, pp. 582-586.

(Continued)

*Primary Examiner* — Randy Gulakowski
*Assistant Examiner* — Kara Boyle
(74) *Attorney, Agent, or Firm* — Venable LLP; Keith G. Haddaway

(57) ABSTRACT

The present disclosure relates to a nail coating system comprising a basecoat, a color layer, and a topcoat. The system of the present disclosure may be applied to natural and/or pre-existing artificial nail coatings. The present disclosure relates generally to compositions for natural and artificial nail coatings, and particularly, but not by way of limitation, to polymerizable compositions and color layers polymerized therefrom. The disclosure further relates to methods of making a polymerized color layer.

57 Claims, No Drawings

U.S. PATENT DOCUMENTS

| | | | |
|---|---|---|---|
| 5,690,940 | A | 11/1997 | Joo |
| 4,514,527 | A | 12/1997 | Mirle |
| 4,189,365 | A | 1/1998 | Fischer |
| 4,521,550 | A | 2/1998 | Martin |
| 4,574,138 | A | 7/1998 | Sirdesai |
| 4,229,431 | A | 8/1998 | Socci |
| 4,596,260 | A | 10/1998 | Biller |
| 4,692,396 | A | 12/1998 | Schade |
| 5,871,573 | A | 2/1999 | Cook et al. |
| 6,413,696 | B1 | 9/1999 | Ahrndt |
| 4,600,030 | A | 10/1999 | Ellingson |
| 4,666,952 | A | 10/1999 | Steffier |
| 4,682,612 | A | 11/1999 | Sommerfeld |
| 4,704,303 | A | 11/1999 | Cook |
| 4,766,005 | A | 11/1999 | Posey-Dowty |
| 5,985,951 | A * | 11/1999 | Cook ............... 522/88 |
| 4,775,580 | A | 12/1999 | Oxman |
| 4,863,993 | A | 1/2000 | Cowperthwaite |
| 5,026,780 | A | 2/2000 | Anand |
| 5,063,257 | A | 9/2000 | Deguchi |
| 5,118,495 | A | 11/2000 | Jia |
| 6,147,137 | A * | 11/2000 | Jia ................. 523/118 |
| 4,718,957 | A1 | 5/2001 | delaPoterie |
| 5,194,292 | A1 | 5/2001 | Narayan |
| 6,251,520 | B1 | 6/2001 | Blizzard et al. |
| 5,206,011 | A1 | 7/2001 | Shimada |
| 6,254,878 | B1 | 7/2001 | Bednarek et al. |
| 5,219,965 | A1 | 3/2002 | Zahora |
| 4,690,369 | A1 | 5/2002 | Lilley |
| 5,270,351 | A1 | 7/2002 | Pang |
| 5,328,725 | A1 | 7/2002 | McComas |
| 4,867,680 | A1 | 10/2002 | Williams |
| 5,338,769 | A1 | 11/2002 | Lilley |
| 5,071,888 | A1 | 1/2003 | Hirota |
| 5,127,414 | A1 | 7/2003 | Lehmann |
| 5,407,666 | A1 | 7/2003 | Lilley |
| 5,177,120 | A1 | 11/2003 | Montgomery |
| 5,424,061 | A1 | 2/2004 | Licata |
| 5,426,166 | A1 | 6/2004 | Yamana |
| 5,435,994 | A1 | 10/2004 | Lilley |
| 5,456,905 | A1 | 11/2004 | Schoon |
| 5,229,431 | A1 | 12/2004 | Williams |
| 5,484,864 | A1 | 12/2004 | Williams |
| 5,314,683 | A1 | 1/2006 | Shin |
| 5,344,583 | A1 | 2/2006 | Lai |
| 5,516,509 | A1 | 6/2006 | Kakino |
| 5,415,903 | A1 | 8/2006 | Qian |
| 5,698,371 | A1 | 8/2006 | Ong |
| 7,125,591 | B2 | 10/2006 | Nakajima et al. |
| 5,453,451 | A1 | 1/2007 | Yan |
| 5,637,292 | A1 | 5/2007 | Rach |
| 5,662,891 | A1 | 5/2007 | Kessel |
| 5,720,804 | A1 | 12/2007 | Rach |
| 5,785,958 | A1 | 4/2008 | Barr |
| 5,849,853 | A1 | 5/2008 | Schmidt |
| 5,708,052 | A1 | 6/2008 | Oshima |
| 5,792,447 | A1 | 7/2008 | Utterodt |
| 5,824,373 | A1 | 9/2008 | Eu |
| 5,965,111 | A1 | 10/2008 | Schoon |
| 5,965,147 | A1 | 4/2009 | Meyer |
| 5,994,530 | A1 | 4/2009 | Klare |
| 5,998,495 | A1 | 9/2009 | Hayes |
| 6,015,549 | A1 | 11/2009 | Radcliffe |
| 5,985,998 | A1 | 1/2010 | Oshima |
| 6,020,402 | A1 | 1/2010 | McCabe |
| 6,391,938 | B1 | 4/2010 | Yonezu |
| 6,121,381 | A1 | 5/2010 | Ito |
| 6,239,189 | B1 | 5/2010 | Schwantes |
| 6,255,034 | B1 | 10/2010 | Nakamura |
| 2002/0156144 | A | 6/1985 | Bowen |
| 2003/0019501 | A | 3/1986 | Moran, Jr. |
| 2003/0134932 | A | 9/1987 | Uchida |
| 2004/0249014 | A | 8/1988 | Montgomery |
| 2006/0005772 | A | 10/1988 | Dighton |
| 2006/0039939 | A | 9/1989 | Montgomery |
| 2006/0189728 | A | 6/1991 | Takizawa |
| 2007/0021533 | A | 11/1991 | Akahane |
| 2007/0099119 | A | 6/1992 | Nafziger |
| 2007/0106017 | A | 3/1993 | Billings |
| 2008/0149270 | A | 4/1993 | Pappas |
| 2008/0167399 | A | 6/1993 | Valint, Jr. |
| 2008/0213506 | A | 12/1993 | Bowen |
| 2008/0241083 | A | 7/1994 | Sato |
| 2009/0086492 | A | 8/1994 | Miyamoto |
| 2010/0012263 | A | 4/1995 | Patel |
| 2010/0105289 | A | 6/1995 | Pappas |
| 2001/0007676 | A1 | 7/2001 | Mui et al. |
| 2003/0175225 | A1 | 9/2003 | Leacock et al. |
| 2003/0220416 | A1 * | 11/2003 | Montgomery et al. ....... 523/122 |
| 2005/0002878 | A1 | 1/2005 | Lefrancois et al. |
| 2006/0128833 | A1 | 6/2006 | Itoh et al. |
| 2009/0220436 | A1 | 9/2009 | Anderson et al. |
| 2011/0045036 | A1 | 2/2011 | Lintner et al. |

FOREIGN PATENT DOCUMENTS

| | | |
|---|---|---|
| EP | 0426085 | 5/1992 |
| EP | 0545116 | 6/1993 |
| EP | 943310 | 3/2002 |
| EP | 1479364 | 11/2004 |
| EP | 1450755 | 8/2008 |
| GB | 656264 | 8/1951 |
| JP | 5271460 | 10/1993 |
| KR | 970002606 | 3/1997 |
| WO | 9312759 | 7/1993 |
| WO | 9848769 | 11/1998 |
| WO | 9955290 | 11/1999 |
| WO | 0236637 | 5/2002 |
| WO | 2004030801 | 4/2004 |
| WO | 2008082929 | 7/2008 |
| WO | 2009005975 | 1/2009 |
| WO | 2011011304 | 1/2011 |

OTHER PUBLICATIONS

International Search Report for PCT International Application No. PCT/US2010/047165, mailed Feb. 25, 2011.
International Search Report for PCT International Application No. PCT/US2010/047169, mailed Nov. 9, 2010.
International Search Report for PCT International Application No. PCT/US2011/027455, mailed May 9, 2011.
Data Sheet for Diurethane Dimethacrylate from Esstech, Inc., 2011.
Data Sheet for Polypropylene Glycol Monomethacrylate. Sartomer. 2011.
International Preliminary Report on Patentability issued in International Application No. PCT/US2010/047169 dated Apr. 11, 2012.
International Preliminary Report on Patentability issued in International Application No. PCT/US2010/047165 dated Mar. 13, 2012.
International Preliminary Report on Patentability issued in International Application No. PCT/US2010/047171 dated Apr. 11, 2012.
Office Action issued in U.S. Appl. No. 12/555,571 dated May 17, 2011.
Office Action issued in U.S. Appl. No. 12/555,571 dated Oct. 26, 2011.
Office Action issued in U.S. Appl. No. 12/573,633 dated Feb. 13, 2012.
Office Action issued in U.S. Appl. No. 12/573,633 dated May 24, 2011.
Office Action issued in U.S. Appl. No. 12/573,640 dated Aug. 15, 2012.
Office Action issued in U.S. Appl. No. 13/079,261 dated Jun. 14, 2012.
Office Action issued in U.S. Appl. No. 13/079,261 dated Oct. 14, 2011.

* cited by examiner

REMOVABLE COLOR LAYER FOR ARTIFICIAL NAIL COATINGS AND METHODS THEREFORE

RELATED APPLICATION

This application is a continuation of U.S. application Ser. No. 12/573,633 filed Oct. 5, 2009 the content of which is incorporated herein by reference in its entirety.

FIELD OF THE INVENTION

The present disclosure relates generally to compositions for nail coatings, and particularly, but not by way of limitation, to polymerizable compositions and color layers polymerized therefrom.

BACKGROUND

The information provided below is not admitted to be prior art to the present invention, but is provided solely to assist the understanding of the reader.

Artificial fingernail and toenail compositions in the form of nail coatings and extenders are well known and have become a major product line in the appearance and beauty industry. The appearance of one's fingernails (and in many cases also toenails) has become of importance to many fashion conscious individuals. Commercial artificial nail compositions have been used to enhance the appearance of natural nails and also to enhance the physical properties of natural nails, including strengthening fragile nail surfaces.

Conventional natural nail coatings may be classified into two categories: nail polishes; also known as lacquers, varnish or enamels and artificial nails; also known as gels or acrylics. Nail polishes typically comprise various solid components which are dissolved and/or suspended in non-reactive solvents. Upon application and drying, the solids deposit on the nail surface as a clear, translucent or colored film. Typically, nail polishes are easily scratched and are easily removable with solvent, usually within one minute and if not removed as described, will chip or peel from the natural nail in one to five days.

Conventional artificial nails are comprised of chemically reactive monomers, and/or oligomers, in combination with reactive or non-reactive polymers to create systems which are typically 100% solids and do not require non-reactive solvents. Upon pre-mixing and subsequent application to the nail plate, or application and exposure to UV radiation, a chemical reaction ensues resulting in the formation of a long lasting, highly durable cross-linked thermoset nail coating that is difficult to remove. Artificial nails may possess greatly enhanced adhesion, durability, as well as scratch and solvent resistance when compared to nail polishes. However, because of these inherent properties, such thermosets are much harder to remove, should the consumer so desire. Removal typically requires soaking in non-reactive solvents for 30-90 minutes (for acrylics and currently available "soakable gels"; it may take more than 90 minutes to remove traditional UV nail gels by solvent) and typically may also require heavily abrading the surface of the artificial coating or scrapping with a wooden or metal probe to assist the removal process.

There remains a need for a cosmetic product that possesses the enhanced adhesion properties of thermosets and also possesses the ease of removal more similar to that of polishes.

The present disclosure forms part of a nail coating system comprising a reactive basecoat adhesion layer (Application Ser. No. 12/555,571 (US 2011/0060065), the present disclosure, an intermediate, decorative and reactive color layer (Application Ser. No. 12/573,633, US 2011/0081306), and a protective and reactive topcoat (Application Ser. No. 12/573,640, US 2011/0082228). The contents of each application are mutually incorporated into each of the others by reference for all purposes.

Other objects and advantages will become apparent from the following disclosure.

SUMMARY OF INVENTION

Aspects of the present disclosure when taken in conjunction with the related disclosures provide a basecoat characterized by firm adhesion to a nail surface combined with a solvent-induced "unzipping," "quick-release" feature that affords facile removal. Aspects of the present disclosure when taken in conjunction with the related disclosures provide a color layer characterized by firm adhesion to polymer surfaces combined with a solvent-induced "unzipping," "quick-release" feature that affords facile removal. Further aspects of the present disclosure when taken in conjunction with the related disclosures provide a protective topcoat characterized by firm adhesion to polymer surfaces combined with a solvent-induced "unzipping," "quick-release" feature that affords facile removal.

An aspect of the present disclosure provides a nail coating comprising a 3-dimentional (3-D) thermoset lattice interpenetrated by a network comprising an organic solvent-dissolvable resin. According to an aspect of the disclosure, the 3-D thermoset lattice provides the enhanced adhesion, toughness, and scratch-resistance of conventional artificial nails. According to an aspect of the disclosure, an interconnected system of voids and an interpenetrating network of an organic solvent-dissolvable resin provides the ease of solvent removability.

According to an aspect, the present disclosure provides a liquid composition comprising at least one monomer, and/or oligomer, and/or polymer which polymerize to a 3-D thermoset. According to an aspect, the present disclosure provides a liquid composition comprising at least one organic solvent-dissolvable resin. According to an aspect, the organic solvent-dissolvable resin forms a network of inclusions within the 3-D thermoset lattice.

According to an aspect, the present disclosure provides a viscous liquid composition comprised of one or more addition-polymerizable, ethylenically-unsaturated monomers.

According to an aspect, the present disclosure provides a monomer which confers the "unzipping" property of ease of removal of the polymerized lattice. According to an aspect, the monomer may be polypropylene glycol-4-monomethacrylate (PPG4 monomethacrylate). According to an aspect, suitable monomers may include any acrylated or methacrylated monomer in the polyethylene glycol (PEG) or polyopropylene glycol (PPG) families. According to an aspect, the "unzipping" monomers are present at from about 0 to about 70 weight % (wt %).

According to an aspect, the liquid composition comprises reactive monomers, and/or oligomers, and/or polymers which provides the polymerized composition increased adhesion. According to an aspect, such reactive monomers, and/or oligomers, and/or polymers may be a (meth)acrylate. As is known to persons of skill in the polymer arts, the term (meth)acrylate encompasses acrylates and/or methacrylates.

According to an aspect, such reactive monomers, and/or oligomers, and/or polymers may be selected from the group consisting of hydroxyethylmethacrylate (HEMA), hydroxypropylmethacrylate (HPMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, acetoacetoxy ethyl methacylate (AAEMA), and mixtures thereof. According to an aspect, such reactive monomers, and/or oligomers, and/or polymers may possess acidic functionality. According to an aspect, the monomer, oligomer or polymer which provides the polymerized composition increased adhesiveness is present from about 0 to about 50 wt %.

An aspect of the present disclosure provides a polymerizable liquid composition comprising a non-reactive, solvent-dissolvable polymer. According to an aspect, the non-reactive, solvent-dissolvable polymer is a cellulose ester. According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. According to a further aspect, the ingredient which provides for ease of removal may be present at from about 0.1 to about 75 wt %.

According to an aspect of the disclosure, the color layer composition may comprise up to 10 wt % of pigments and/or dyes.

An aspect of the present disclosure provides methods of removal. According to an aspect, the thermoset polymerized from the disclosed composition is provided an increased sensitivity to organic solvents and, in particular, to acetone. According to an aspect of the disclosure, means are provided to distribute organic solvent to the polymer/natural nail interface. According to an aspect, delivering an appropriate solvent to the polymer/natural nail interface will result in an unzipping effect which leads to rapid disruption of the adhesive bond interface and greatly facilitates quick and gentle removal from the natural nail.

Still other aspects and advantages of the present invention will become readily apparent by those skilled in the art from the following detailed description, wherein it is shown and described preferred embodiments of the invention, simply by way of illustration of the best mode contemplated of carrying out the invention. As will be realized, the invention is capable of other and different embodiments, and its several details are capable of modifications in various obvious respects, without departing from the invention. Accordingly, the description is to be regarded as illustrative in nature and not as restrictive.

BRIEF DESCRIPTION OF DRAWINGS

Not Applicable.

DETAILED DESCRIPTION OF A PREFERRED EMBODIMENT

Nail coatings commonly consist of a material applied to a keratin nail surface. Prior art coatings may damage the nail by at least two mechanisms. First, adequate adhesion of the enhancement to the natural nail may require abrasion to roughen the nail surface. And second, removal of the enhancement may require prolonged exposure to possibly damaging solvents and or further abrasion of the artificial nail surface.

An embodiment of the present disclosure provides a nail coating comprising a 3-dimentional (3-D) thermoset lattice interpenetrated by a network comprising an organic solvent-dissolvable resin. According to an aspect of the disclosure, a 3-D thermoset lattice provides the enhanced adhesion, toughness, and scratch-resistance of conventional artificial nails. According to an embodiment, a basecoat is interposed between the natural nail surface and the present color layer.

The terms "nail" and "nail surface" mean the natural, keratinous nail surface, or a natural nail to which a pre-formed artificial nail or nail tip is adhered. In other words, the polymerizable compositions of the invention may be applied directly to the keratinous surface of the natural nail, or to a nail surface having affixed thereto a pre-formed artificial nail or nail tip enhancement.

The invention comprises a polymerizable composition for application to the nails and polymerization thereon to yield an artificial nail structure. The polymerizable composition is preferably an anhydrous liquid, having the consistency of a semi-mobile gel to freely mobile liquid at room temperature. Immediately prior to use, the polymerizable composition is applied to the nail surface and shaped by the nail technician. After polymerization an artificial nail structure is obtained.

An embodiment of the liquid composition comprises reactive monomers, and/or oligomers, and/or polymers which provides the polymerized composition increased adhesion. In certain embodiments, such reactive monomers, and/or oligomers, and/or polymers may be a (meth)acrylate. As is known to persons of skill in the polymer arts, the term (meth)acrylate encompasses acrylates and/or methacrylates. According to an aspect, such reactive monomers, and/or oligomers, and/or polymers may be selected from the group consisting of hydroxypropyl methacrylate (HPMA), hydroxyethyl methacrylate (HEMA), EMA, THFMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, acetoacetoxy ethyl methacrylate (AAEMA), and mixtures thereof. According to an aspect, such reactive monomers, and/or oligomers, and/or polymers may possess acidic functionality. According to an aspect, the monomer, oligomer or polymer which provides the polymerized composition increased adhesiveness is present from about 0 to about 50 wt %.

The ethylenically unsaturated reactant may be mono-, di-, tri-, or poly-functional as regards the addition-polymerizable ethylenic bonds. A variety of ethylenically unsaturated reactants are suitable, so long as the reactants are capable of polymerization to yield a polymerized artificial nail structure upon exposure to the appropriate stimuli. Suitable ethylenically unsaturated reactants are disclosed in U.S. Pat. No. 6,818,207 which is incorporated by reference.

Certain embodiments of the liquid composition comprise at least one monomer which confers the "unzipping" property by imparting to the interfacial bonds a sensitivity to organic solvent. According to an aspect, the at least one monomer may be polypropylene glycol-4-monomethacrylate (PPG4 monomethacrylate). According to an aspect, suitable monomers may include any acrylated or methacrylated monomer in the PPG or polyethylene glycol (PEG) family. According to an aspect, the "unzipping" monomers are present at from about 0 to about 70 weight % (wt %).

An embodiment of the present disclosure provides a polymerizable liquid composition comprising a methacrylate monomer which provides improved adhesion, viscosity, wear and durability. In certain embodiments, the methacrylate monomer is a tetrahydrofurfural methacrylate. In other embodiments, some or all of the tetrahydrofurfural methacrylate may be substituted by such monomers including, but not limited to ethyl methacrylate (EMA), HPMA, and other monomers such as pyromellitic dianhydride glyceryl dimethacrylate, and similar (meth)acrylate monomers. The methacrylate monomer may be present from about 0 to about 70 wt %.

Certain embodiments of the polymerizable liquid composition of the present disclosure may comprise a urethane (meth)acrylate resin which may convey flexibility and toughness to the polymerized product. In certain embodiments, urethane methacrylates are preferred. The urethane (meth) acrylate monomer may be present from about 0 to about 50 wt %. In certain embodiments, the urethane (meth)acrylate may have a molecular weight (grams/mole) of from about 100 to about 20,000. In certain embodiments, the urethane (meth) acrylate may have a molecular weight of from about 300 to about 15,000. In certain embodiments, the urethane (meth) acrylate may have a molecular weight of from about 500 to about 13,000. In certain embodiments, the urethane (meth) acrylate may have a molecular weight of from about 500 to about 6,000.

In certain embodiments of the disclosure, the 3-D thermoset lattice is interpenetrated by a network of voids left by the evolution of a non-reactive solvent. During the curing process, domains of a non-reactive, organic solvent-dissolvable resin form within the crosslinked polymer matrix. When it is desired to remove the nail covering, the polymer is exposed to a solvent which penetrates the network of voids to the domains of the solvent-dissolvable resin. Dissolution of the resin allows further penetration of solvent to the interior of the thermoset and also to the basecoat/color layer interface.

Certain embodiments of the polymerizable liquid composition of the present disclosure may comprise a non-reactive, solvent-dissolvable polymer. According to an aspect, the non-reactive, solvent-dissolvable polymer is a cellulose ester. According to a particular aspect, the non-reactive, solvent-dissolvable polymer is a cellulose acetate alkylate. According to a more particular aspect, the non-reactive, solvent-dissolvable polymer is a cellulose acetate butyrate or a cellulose acetate propionate. The non-reactive, solvent-dissolvable polymer may be a mixture of any acceptable non-reactive, solvent-dissolvable polymer. According to a further aspect, the non-reactive, solvent-dissolvable polymer may be present at from about 0.1 to about 75 wt %.

According to certain embodiments, the color layer further comprises at least one rheology modifying agent. In certain embodiments, the rheology modifier is present at up to 10 wt %. In certain embodiments the rheology agent may be present to provide a thixotropic property to the composition to aid in the suspension of pigment particles. In certain embodiments, the rheology agent may be a fumed silica. In certain embodiments, the rheology agent may be a polyamide.

The compositions of the invention may contain from about 0.001-5% by weight of a plasticizer. The plasticizer causes the polymerized nail structure to have improved flexibility and reduced brittleness. Suitable plasticizers may be esters, low volatility solvents, or non-ionic materials such as non-ionic organic surfactants or silicones.

Suitable esters include those having the general structure RCO—OR' where RCO— represents a carboxylic acid radical and where —OR' is an alcohol residue. Preferably R and R' are fatty radicals, having 6 to 30 carbon atoms, and may be saturated or unsaturated. Examples of suitable esters are those set forth on pages 1558 to 1564 of the C.T.F.A. Cosmetic Ingredient Dictionary and Handbook, Seventh Edition, 1997, which is hereby incorporated by reference. In the preferred compositions of the invention, the plasticizer is an ester of the formula RCO—OR' wherein R and R' are each independently a straight or branched chain $C_{6-30}$ alkyl. A suitable plasticizer is isostearyl isononanoate. Other suitable plasticizers are disclosed in U.S. Pat. No. 6,818,207 which is incorporated by reference.

According to certain embodiments, the color layer further comprises at least one UV stabilizing agent. In certain embodiments, the UV stabilizer is present at up to 2 wt %.

The compositions of the invention may contain one or more U.V. absorbers, which assist in reducing the yellowing which is often seen in artificial nails. U.V. absorbers have the ability to convert incident U.V. radiation into less damaging infrared radiation (heat), or visible light. A recommended amount of U.V. absorber is 0.001-5% by weight of the total composition. Suitable U.V. absorbers include hydroxy benzotriazole compounds and benzophenone compounds such as are disclosed in U.S. Pat. No. 6,818,207, incorporated by reference.

It may be desirable to include one or more polymerization regulators. A polymerization regulator assists in preventing the polymerization of the monomer composition from occurring too quickly. Hydroquinone and similar materials are suitable polymerization regulators. Suggested ranges of polymerization regulators are from about 0.0001-5% by weight of the total composition. Suitable polymerization regulators are disclosed in U.S. Pat. No. 6,818,207, incorporated by reference.

Without being bound by theory, the present inventors eases removal of the nail covering by facilitating entrance of solvent into the interior of the coating. Conventional polymerized nail coatings are weakened by surface abrasion followed by long-term (30 to 90 minute) exposure to organic solvents. The solvent slowly seeps in at the outer surface and edges of the thermoset and eventually swells the coating. The swelling eventually weakens the entire matrix structure, as well as disrupts adhesion to the nail surface. Even a weakly attached nail coating may require abrasion to enhance solvent penetration and speed removal. However, the slow rate at which solvent diffuses through the thermoset, limits the rate of swelling.

The present invention provides a 3-D thermoset interpenetrated by a network of solvent-dissolvable channels and inclusions. Upon exposure to organic solvent, the cellulose ester, or other non-reactive, organic solvent-soluble polymer, is dissolved and leached from the coating. The result is a series of solvent accessible passageways riddled throughout the thermoset. Under these conditions, solvent may attack the interior of the thermoset no longer limited by a slow diffusion rate.

Certain embodiments of the disclosed polymerizable composition may be viscous gels or liquids. Gel or liquid embodiments may be polymerized by exposure to radiant energy, such as heat, visible, U.V., or electron-beam radiation. Liquid or gel embodiments are applied upon nails and may be shaped to the desired configuration. The coated nails are exposed to radiant energy, and polymerization occurs.

The inventive composition may be polymerizable with actinic radiation. The actinic radiation may be visible, ultraviolet (UV), or electron beam radiation. The UV radiation may be characterized by a wavelength, or group of wavelengths, typically, but not limited to about 320 to about 420 nanometers.

After the liquid composition is applied to a surface, especially a basecoat surface, the liquid is cured. The liquid composition comprises ethylenic unsaturated (meth)acrylates which and may be cured by a UV-initiated, free-radical polymerization method. Persons of skill in the polymerization arts may readily determine suitable photoinitiators for use with the invention. Set forth below are non-limiting representative photoinitiators that are suitable for purposes of the invention.

A non-limiting suitable photoinitiator is a 2,4,6-trimethylbenzoyldiphenylphosphorous derivative. A suitable derivative is ethyl-2,4,6-trimethylbenzoyldiphenylphosphinate, which may be obtained under the tradename Lucirin® TPO-L (BASF Aktiengesellschaft, Ludwigshafen, DE). Another non-limiting suitable derivative is 2,4,6-Trimethylbenzoyldiphenylphosphine oxide, which may be obtained under the trade name Lucerin® (BASF) or as Genocure® TPO (Rahn) The 2,4,6-trimethylbenzoyldiphenylphosphinate photoinitiator may be present from about 0% to about 20 wt %.

A non-limiting suitable photoinitiator is hydroxycyclohexyl phenyl ketone, which may be obtained under the tradename Igracure® 184 and which may be present from about 0 to about 20 wt %.

A non-limiting suitable photoinitiator is benzil dimethyl ketal (BDK), which may be obtained under the tradename FIRSTCURE® BDK (Albemarle, Baton Rouge, La., US) and which may be present from about 0 to about 20 wt %.

Certain embodiments of the disclosed color layer may comprise up to 10 wt % pigments and/or dyes. Embodiments of the related basecoat and topcoat disclosures may have up to 1 wt % pigments and or dyes. High concentrations of pigments and/or dyes may absorb UV radiation. To compensate therefore, certain embodiments of the present disclosure may comprise higher concentrations, up to 20 wt %. photoinitiator.

A conventional thermoset nail coating comprises 100% solids and does not comprise nonreactive solvent. The polymerizable liquid composition of the present disclosure further comprises at least one non-reactive solvent. A suitable non-reactive solvent is readily volatile at room temperature and is a good solvent for the remaining ingredients. Upon application, the non-reactive solvent readily volatilizes leaving regions of increased porosity. These porous regions later facilitate the entry of a remover solvent which may be acetone.

Suitable non-reactive solvents include, but are not limited to ketones, alkyl acetates, alcohols, alkanes, alkenes, and mixtures thereof. Suitable non-reactive solvents may be selected from the group consisting of acetone, ethyl acetate, butyl acetate, isopropyl alcohol, ethanol, methyl ethyl ketone, toluene, hexane, and mixtures thereof. A particularly suitable non-reactive solvent is acetone. Typically a non-reactive solvent or a mixture of non-reactive solvents is included at up to about 70 weight percent.

Certain embodiments of the formulation may optionally comprise (meth)acrylate monomers and/or polymers in order to fine tune adhesion and removal properties. Non-limiting examples of such (meth)acrylates include: mono or poly (meth)acrylates, HPMA, HEMA, pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, ethyl methacrylate, tetrahydrofurfuryl methacrylate, butyl methacrylate, isobutyl methacrylate, PEG-4 dimethacrylate, PPG monomethacrylate, trimethylolpropane trimethacrylate, hydoxyethyl methacrylate, isopropylidenediphenyl bisglycidyl methacrylate, lauryl methacrylate, cyclohexyl methacrylate, hexyl methacrylate, urethane methacrylate, hydroxypropyl methacrylate, triethylene glycol dimethacrylate, ethylene glycol dimethacrylate, tetraethylene glycol dimethacrylate, trimethylolpropane trimethacrylate, neopentylglycol dimethacrylate, acetoacetoxy ethyl methacylate (AAEMA), and mixtures thereof.

Certain embodiments of the formulation may optionally comprise resins, such as, but not limited to polyvinylbutyral and/or tosylamide formaldehyde resins. Such resins may also act as film formers, adhesion promoters, and aids to removal. These resins may also qualify as solvent-dissolvable resins which can be extracted to create channels for solvent absorption and migration.

Certain embodiments of the formulation may optionally comprise plasticizers, such as, but not limited to diisobutyl adipate. Plasticizers act to minimize the effects of brittleness of the subsequently formed polymer after exposure to UV sun light and air. Plasticizers also are found to slightly shorten the removal time. Plasticizers may be present at from 0 to about 25 wt %. Persons of skill in the polymer arts will appreciate that inclusion of plasticizers above a certain limit is undesirable because they may impare the integrity and durability of the coatings.

The unpolymerized color layer may have the consistency of a liquid or gel. The unpolymerized color layer may be applied to an polymerized basecoat surface. In an embodiment the polymerized basecoat may be an embodiment of co-pending U.S. application Ser. No. 12/555,571 (US 2011/0060065). The polymerized basecoat may be applied to a nail surface and contacted with a color layer. The nail surface-basecoat-color layer system may be exposed to UV radiation. The basecoat and color layer may be polymerized thereby adhering the color layer to the nail surface.

In an embodiment, a color layer may be removed from the natural nail surface without abrading the artificial nail surface.

As compared to conventional nail coatings, the present disclosure relates to a major advantage in that it enables the durable color layer to adhere to the natural nail for periods in excess of two weeks without breakdown of the coating. In contrast to conventional coatings, the present disclosure relates to a UV gel system that is non-damaging to the natural nail. The application process requires no abrasive treatment of the natural nail. And the process of removal at most calls for the use of a light touch of a wooden stick. Moreover, in comparison to conventional systems, the present disclosure relates to a more rapidly removable nail coating system achieving removal in 20 seconds for basecoat alone to 20 minutes for the whole system.

The polymerized basecoat of the present invention may adhere to the keratin nail surface by means of hydrogen bonds. The basecoat and color layer may be removed from the nail surface by means of organic solvents. Non-limiting solvents include acetone, butyl acetate, isopropyl alcohol, ethanol, ethyl acetate, methyl ethyl ketone, and mixtures thereof.

Another Ethylenically Unsaturated Monomer

The polymerizable composition preferably contains 5-98%, preferably 10-96%, more preferably 25-95% by weight of the total composition of at least one other ethylenically unsaturated monomer. The ethylenically unsaturated monomer may be mono-, di-, tri-, or polyfunctional as regards the addition-polymerizable ethylenic bonds. A variety of ethylenically unsaturated monomers are suitable, so long as the monomers selected are capable of polymerization directly on the nail surface to yield a polymerized artificial nail structure upon exposure to the appropriate stimuli.

Examples of suitable monofunctional ethylenically unsaturated monomers include those of the formula: I.

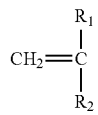

wherein $R_1$ is H, a $C_{1-30}$ straight or branched chain alkyl, aryl, aralkyl; $R_2$ is a pyrrolidone, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl, pyrrolidone, or a substituted or unsubstituted aromatic, alicylic, or bicyclic ring where the substitutents are $C_{1-30}$ straight or branched chain alkyl which may be substituted with one or more hydroxyl groups, or $[(CH_2)_mO]_nH$ wherein m is 1-20, and n is 1-200.

Preferably, the monofunctional ethylenically unsaturated monomer is of Formula I, above, wherein $R_1$ is H or a $C_{1-30}$ alkyl, and $R_2$ is COOM wherein M is a $C_{1-30}$ straight or branched chain alkyl which may be substituted with one or more hydroxy groups.

More preferably, $R_1$ is H or $CH_3$, and $R_2$ is COOM wherein M is a $C_1$-10 straight or branched chain alkyl which may be substituted with one or more hydroxy groups. In the preferred embodiment of the invention, the monofunctional ethylenically unsaturated monomer is a mixture of monomers of Formula I where in one monomer $R_1$ is H or $CH_3$ and $R_2$ is COOM where M is a $C_{1-10}$ alkyl, and where in the second monomer $R_1$ is H or $CH_3$, and $R_2$ is COOM where M is a $C_{1-10}$ alkyl substituted with one or more hydroxy groups.

In the preferred embodiment of the invention, the monofunctional ethylenically unsaturated monomer comprises a mixture of one or more methacrylate monomers and one or more hydroxyalkyl methacrylate monomers, preferably about 50-98.5% of a methacrylate monomer, and 5-20% of a hydroxyalkyl methacrylate monomer. Most preferred is a composition containing 60-98.5% ethyl methacrylate and 7-15% hydroxypropylmethacrylate.

Di-, tri- and polyfunctional monomers, as well as oligomers, of the above monofunctional monomers may also be used in the composition. Such di-, tri-, and polyfunctional monomers are generally known as cross-linking monomers because they aid in cross-linking of the monomer composition during and after polymerization. Preferred difunctional monomers include those having the general formula:

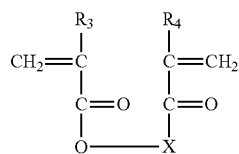

wherein $R_3$ and $R_4$ are each independently H, a $C_{1-30}$ straight or branched chain alkyl, aryl, or aralkyl; and X is $[(CH_2)_xO_y]_z$ wherein x is 1-20, and y is 1-20, and z is 1-100. Particularly preferred are difunctional acrylates and methacrylates, such as the compound of formula II above wherein $R_3$ and $R_4$ are $CH_3$ and X is $[(CH_2)_xO_y]_z$ wherein x is 1-4; and y is 1-6; and z is 1-10.

Particularly preferred are difunctional acrylates and methacrylates, such as the compound of formula II above wherein $R_3$ and $R_4$ are $CH_3$ and X is $[(CH_2)_xO_y]_z$ wherein x is 2; and y is 1, and z is 4. The polymerizable compositions preferably contain 0.1-25%, preferably 0.5-20%, more preferably 1-15% by weight of a difunctional monomer. Particularly preferred is where the difunctional monomer is an ethylene glycol dimethacrylate. Most preferred is where the difunctional monomer is tetraethylene glycol dimethacrylate.

Trifunctional and polyfunctional monomers are also suitable for use in the polymerizable monomer compositions of the invention. Examples of such monomers include acrylates and methacrylates such as trimethylolpropane trimethacrylate or trimethylolpropane triacrylate. The preferred compositions of the invention contain 0.001-5%, preferably 0.005-4%, more preferably 0.01-3% by weight of a polyfunctional monomer such as trimethylolpropane trimethacrylate ester or trimethylolpropane triacrylate ester.

EXAMPLE 1

Chemical Resistance Test

To compare chemical resistance a topcoat formulation according to the present disclosure was compared against a commercial polish topcoat formulation and a commercial enhancement type topcoat formulation. We employed the conventional MEK double rub test except that acetone substituted for the methyl ethyl ketone. Thin films of each formulation were prepared on glass microscope slides. Each film was formed to a 5 mil wet thickness. The commercial enhancement type formulation and the formulation of the present disclosure were cured by exposure to UV light using a Brisa™ lamp. A very thin, unpolymerized tacky top layer was wiped to dryness using 99 wt % isopropanol. The polish formulation was not cured, but was dried under ambient conditions. All specimens were aged under conditions of ambient light and temperature for 24 hours. Following aging, each sample was individually rubbed with cotton pads soaked in 99 wt % acetone. The polish formulation was completely removed by two rubs. The formulation of the present invention was dulled by two rubs, but remained intact for at least 150 rubs. The enhancement formulation remained shiny and intact for at least 200 rubs.

EXAMPLE 2

Pencil Hardness Test

To test scratch resistant, we recorded the lowest "H" number of the pencil which dented test samples prepared as given in Example 1. We also recorded the lowest "H" number of the pencil capable of tearing test films. The polish formulation was dented and torn by 3H and 4H pencils, respectively. The formula of the present disclosure was dented and torn respectively by 3H and 6H pencils. The enhancement formula was dented by a 4H pencil and was not torn even by the hardest pencil (6H). This test showed that the present disclosure had a significant better scratch resistance than the nail polish formula.

INDUSTRIAL UTILITY

This invention has industrial applicability in providing compositions and methods for improving the adhesion of nail coatings to natural nails without requiring abrasion of the natural nail. The invention further provides means for removing a nail coating without requiring abrasion of the natural nail surface or extended removal times soaking in a solvent.

The invention claimed is:

1. A polymerizable composition comprising:
   at least one first reactive (meth)acrylate monomer comprising HPMA;
   at least one second reactive (meth)acrylate monomer selected from the group consisting of hydroxyethylmethacrylate (HEMA), hydroxypropylmethacrylate (HPMA), ethyl methacrylate (EMA), tetrahydrofurfuryl methacrylate (THFMA), pyromellitic dianhydride di(meth)acrylate, pyromellitic dianhydride glyceryl dimethacrylate, pyromellitic dimethacrylate, methacroyloxyethyl maleate, 2-hydroxyethyl methacrylate/succinate, 1,3-glycerol dimethacrylate/succinate adduct, phthalic acid monoethyl methacrylate, acetoacetoxy ethyl methacylate (AAEMA), and mixtures thereof;
   at least one reactive urethane (meth)acrylate;
   at least one addition-polymerizable, ethylenically-unsaturated monomer;
   at least one non-reactive, solvent-dissolvable polymer; and
   at least one non-reactive solvent;
   wherein upon exposure to a polymerization accelerant, said polymerizable composition cures to an acrylic thermoset having voids defined therein.

2. The polymerizable composition according to claim 1, further comprising at least one compound selected from the group consisting of polypropylene glycol monomethacrylates, polyethylene glycol monomethacrylates, and mixtures thereof.

3. The polymerizable composition according to claim 1, wherein said polymerization accelerant is selected from the group consisting of thermal conduction and/or radiation, visible radiation, UV radiation, electron beam radiation, amines, peroxides, and combinations thereof.

4. The polymerizable composition of claim 1, wherein said at least one non-reactive, solvent-dissolvable polymer is a cellulose ester.

5. The polymerizable composition of claim 4, wherein said cellulose ester is a cellulose acetate alkylate.

6. The polymerizable composition of claim 5, wherein said cellulose acetate alkylate is selected from the group consisting of cellulose acetate butyrate, cellulose acetate propionate, and mixtures thereof.

7. The polymerizable composition of claim 1, wherein said at least one non-reactive, solvent-dissolvable polymer is present at from about 5 to about 70 wt %.

8. The polymerizable composition of claim 1, wherein said at least one non-reactive, solvent-dissolvable polymer is present at from about 10 to about 60 wt %.

9. The polymerizable composition of claim 1, wherein said at least one non-reactive, solvent-dissolvable polymer is present at from about 20 to about 50 wt %.

10. The polymerizable composition according to claim 1, further comprising an adhesion-promoting (meth)acrylate.

11. The polymerizable composition according to claim 10, wherein said adhesion-promoting (meth)acrylate is selected from the group consisting of tetrahydrofurfural methacrylate, ethyl methacrylate, hydroxypropyl methacrylate, pyromellitic dianhydride glyceryl dimethacrylate, and mixtures thereof.

12. The polymerizable composition according to claim 1, further comprising pyromellitic glyceryl dimethacrylate.

13. The polymerizable composition of claim 1, further comprising at least one colorant.

14. The polymerizable composition of claim 1, further comprising at least one rheology agent.

15. The polymerizable composition of claim 14, wherein said at least one rheology agent is a fumed silica.

16. The polymerizable composition of claim 15, wherein a surface of said fumed silica is modified with polydimethylsiloxane.

17. The polymerizable composition of claim 5, wherein said at least one rheology agent is a polyamide.

18. The polymerizable composition of claim 14, wherein said at least one rheology agent present at up to about 10 wt %.

19. The polymerizable composition of claim 1, wherein said at least one at least one urethane (meth)acrylate has a molecular weight of from about 300 to about 1,000.

20. The polymerizable composition of claim 1, wherein said at least one non-reactive solvent is selected from the group consisting of ketones, alkyl acetates, alcohols, alkanes, alkenes, and mixtures thereof.

21. The polymerizable composition of claim 1, wherein said at least one non-reactive solvent is selected from the group consisting of acetone, ethyl acetate, butyl acetate, isopropyl alcohol, ethanol, methyl ethyl ketone, toluene, hexane, and mixtures thereof.

22. The polymerizable composition of claim 1, wherein said at least one non-reactive solvent is acetone.

23. The polymerizable composition of claim 1, wherein said at least one non-reactive solvent is included at up to about 70 weight percent.

24. The polymerizable composition of claim 1, further comprising at least one photoinitiator.

25. The polymerizable composition of claim 24, wherein said at least one photoinitiator is selected from the group consisting of benzoylphenylphosphinates, cyclohexylphenyl ketones, benzyl ketals, and mixtures thereof.

26. A polymerizable composition comprising:
   at least one first reactive (meth)acrylate monomer selected from the group consisting of ethyl methacrylate (EMA), hydroxypropyl methacrylates (HPMA), pyromellitic dianhydride glyceryl dimethacrylate, and mixtures thereof;
   at least one second reactive (meth)acrylate comprising HEMA;
   at least one reactive urethane (meth)acrylate;
   at least one addition-polymerizable, ethylenically-unsaturated monomer;
   at least one non-reactive, solvent-dissolvable polymer; and
   at least one non-reactive solvent;
   wherein upon exposure to a polymerization accelerant, said polymerizable composition cures to an acrylic thermoset having voids defined therein.

27. The polymerizable composition of claim 1, wherein the at least one second reactive (meth)acrylate is HEMA.

28. The polymerizable composition of claim 27, wherein the addition-polymerizable ethylenically unsaturated monomer has the formula:

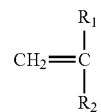

wherein R1 is H, a C1-30 straight or branched chain alkyl, aryl, aralkyl; R2 is a pyrrolidone, or a substituted or unsubstituted aromatic, alicyclic, or bicyclic ring where the substituents are C1-30 straight or branched chain alkyl, or COOM wherein M is H, a C1-30 straight or branched chain alkyl, pyrrolidone, or a substituted or unsubstituted aromatic, alicyclic, or bicyclic ring where the substituents are C1-30 straight or branched chain alkyl which may be substituted with one or more hydroxyl groups, or [(CH2)mO]nH wherein m is 1-20, and n is 1-200.

29. The polymerizable composition of claim 27, wherein the addition-polymerizable ethylenically unsaturated monomer is a difunctional monomer having the formula:

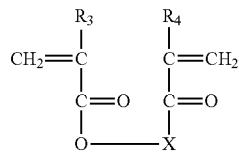

wherein R3 and R4 are each independently H, a C1-30 straight or branch chain alkyl, aryl, or aralkyl; and X is [(CH2)xOy]z wherein x is 1-20, and y is 1-20, and z is 1-100.

30. The polymerizable composition of claim 27, wherein the addition-polymerizable ethylenically unsaturated monomer is selected from the group consisting of trifunctional acrylates, trifunctional methacrylates, polyfunctional acrylates and polyfunctional methacrylates.

31. The polymerizable composition according to claim 26, further comprising at least one compound selected from the group consisting of polypropylene glycol monomethacrylates, polyethylene glycol monomethacrylates, and mixtures thereof.

32. The polymerizable composition according to claim 26, wherein said polymerization accelerant is selected from the group consisting of thermal conduction and/or radiation, visible radiation, UV radiation, electron beam radiation, amines, peroxides, and combinations thereof.

33. The polymerizable composition of claim 26, wherein said at least one non-reactive, solvent-dissolvable polymer is a cellulose ester.

34. The polymerizable composition of claim 33, wherein said cellulose ester is a cellulose acetate alkylate.

35. The polymerizable composition of claim 34, wherein said cellulose acetate alkylate is selected from the group consisting of cellulose acetate butyrate, cellulose acetate propionate, and mixtures thereof.

36. The polymerizable composition of claim 26, wherein said at least one non-reactive, solvent-dissolvable polymer is present at from about 5 to about 70 wt %.

37. The polymerizable composition of claim 26, wherein said at least one non-reactive, solvent-dissolvable polymer is present at from about 10 to about 60 wt %.

38. The polymerizable composition of claim 26, wherein said at least one non-reactive, solvent-dissolvable polymer is present at from about 20 to about 50 wt %.

39. The polymerizable composition according to claim 26, further comprising an adhesion-promoting (meth)acrylate.

40. The polymerizable composition according to claim 39, wherein said adhesion-promoting (meth)acrylate is selected from the group consisting of tetrahydrofurfural methacrylate, ethyl methacrylate, hydroxypropyl methacrylate, pyromellitic dianhydride glyceryl dimethacrylate, and mixtures thereof.

41. The polymerizable composition according to claim 26, further comprising pyromellitic glyceryl dimethacrylate.

42. The polymerizable composition of claim 26, further comprising at least one colorant.

43. The polymerizable composition of claim 26, further comprising at least one rheology agent.

44. The polymerizable composition of claim 43, wherein said at least one rheology agent is a fumed silica.

45. The polymerizable composition of claim 44, wherein a surface of said fumed silica is modified with polydimethylsiloxane.

46. The polymerizable composition of claim 44, wherein said at least one rheology agent is a polyamide.

47. The polymerizable composition of claim 43, wherein said at least one rheology agent present at up to about 10 wt %.

48. The polymerizable composition of claim 26, wherein said at least one at least one urethane (meth)acrylate has a molecular weight of from about 300 to about 1,000.

49. The polymerizable composition of claim 26, wherein said at least one non-reactive solvent is selected from the group consisting of ketones, alkyl acetates, alcohols, alkanes, alkenes, and mixtures thereof.

50. The polymerizable composition of claim 26, wherein said at least one non-reactive solvent is selected from the group consisting of acetone, ethyl acetate, butyl acetate, isopropyl alcohol, ethanol, methyl ethyl ketone, toluene, hexane, and mixtures thereof.

51. The polymerizable composition of claim 26, wherein said at least one non-reactive solvent is acetone.

52. The polymerizable composition of claim 26, wherein said at least one non-reactive solvent is included at up to about 70 weight percent.

53. The polymerizable composition of claim 26, further comprising at least one photoinitiator.

54. The polymerizable composition of claim 53, wherein said at least one photoinitiator is selected from the group consisting of benzoylphenylphosphinates, cyclohexylphenyl ketones, benzyl ketals, and mixtures thereof.

55. The polymerizable composition of claim 26, wherein the addition-polymerizable ethylenically unsaturated monomer has the formula:

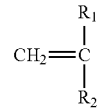

wherein R1 is H, a C1-30 straight or branched chain alkyl, aryl, aralkyl; R2 is a pyrrolidone, or a substituted or unsubstituted aromatic, alicyclic, or bicyclic ring where the substituents are C1-30 straight or branched chain alkyl, or COOM wherein M is H, a C1-30 straight or branched chain alkyl, pyrrolidone, or a substituted or unsubstituted aromatic, alicyclic, or bicyclic ring where the substituents are C1-30 straight or branched chain alkyl which may be substituted with one or more hydroxyl groups, or [(CH2)mO]nH wherein m is 1-20, and n is 1-200.

56. The polymerizable composition of claim 26, wherein the addition-polymerizable ethylenically unsaturated monomer is a difunctional monomer having the formula:

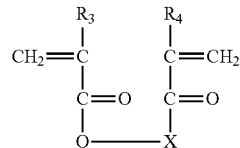

wherein R3 and R4 are each independently H, a C1-30 straight or branch chain alkyl, aryl, or aralkyl; and X is [(CH$_2$)xOy]z wherein x is 1-20, and y is 1-20, and z is 1-100.

57. The polymerizable composition of claim 26, wherein the addition-polymerizable ethylenically unsaturated monomer is selected from the group consisting of trifunctional acrylates, trifunctional methacrylates, polyfunctional acrylates and polyfunctional methacrylates.

* * * * *